(12) United States Patent  
Von Arx et al.

(10) Patent No.: US 8,352,040 B2
(45) Date of Patent: Jan. 8, 2013

(54) DIVERSITY ANTENNA SYSTEM FOR COMMUNICATION WITH AN IMPLANTABLE MEDICAL DEVICE

(75) Inventors: Jeffrey A. Von Arx, Minneapolis, MN (US); Prashant Rawat, Blaine, MN (US); William R. Mass, Maple Grove, MN (US); Greg Carpenter, Centerville, MN (US); Vineel Vallapureddy, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 987 days.

(21) Appl. No.: 11/068,497

(22) Filed: Feb. 28, 2005

(65) Prior Publication Data

US 2006/0195162 A1 Aug. 31, 2006

(51) Int. Cl.
*A61N 1/08* (2006.01)
(52) U.S. Cl. .............................. 607/60; 607/32; 128/903
(58) Field of Classification Search .................... 607/32, 607/60; 128/903
See application file for complete search history.

(56) References Cited

U.S. PATENT DOCUMENTS

| | | | |
|---|---|---|---|
| 4,958,645 A * | 9/1990 | Cadell et al. | 600/484 |
| 5,142,534 A | 8/1992 | Simpson et al. | |
| 5,342,408 A | 8/1994 | deCoriolis et al. | |
| 5,561,673 A | 10/1996 | Takai et al. | |
| 5,787,122 A * | 7/1998 | Suzuki | 375/267 |
| 5,842,135 A | 11/1998 | Ishijima | |
| 6,167,312 A | 12/2000 | Goedeke | |
| 6,169,925 B1 | 1/2001 | Villaseca et al. | |
| 6,226,508 B1 * | 5/2001 | Takahashi et al. | 455/277.1 |
| 6,434,429 B1 | 8/2002 | Kraus et al. | |
| 6,488,704 B1 | 12/2002 | Connelly et al. | |
| 6,490,487 B1 | 12/2002 | Kraus et al. | |
| 6,574,510 B2 | 6/2003 | Von Arx et al. | |
| 6,716,165 B1 | 4/2004 | Flanders et al. | |
| 6,844,854 B2 | 1/2005 | Johnson et al. | |
| 6,889,086 B2 * | 5/2005 | Mass et al. | 607/60 |
| 6,917,833 B2 * | 7/2005 | Denker et al. | 607/32 |
| 7,069,086 B2 | 6/2006 | Von Arx | |
| 7,072,718 B2 | 7/2006 | Von Arx et al. | |
| 7,107,085 B2 | 9/2006 | Doi | |
| 7,610,065 B2 | 10/2009 | Vallapureddy et al. | |

(Continued)

FOREIGN PATENT DOCUMENTS

EP 0744841 A2 11/1996

(Continued)

OTHER PUBLICATIONS

"International Search Report and Written Opinion for Application No. PCT/US2006/006350, dated Jul. 13, 2006", 14 Pages.

(Continued)

*Primary Examiner* — Joseph Dietrich
(74) *Attorney, Agent, or Firm* — Schwegman Lundberg & Woessner, P.A.

(57) ABSTRACT

A system for communicating with an implantable medical device via RF telemetry is disclosed which mitigates the effects of nulls caused by, e.g., multi-path distortion. In one embodiment, signals transmitted by the implantable device to an external device are simultaneously received with a pair of separate spaced apart first and second antennas. The antennas may provide spatial and/or polar diversity. The presence of nulls in the implantable device's transmission pattern can be determined by detecting an error rate in the signals received from the implantable device with each antenna.

20 Claims, 2 Drawing Sheets

U.S. PATENT DOCUMENTS

| | | | |
|---|---|---|---|
| 7,925,356 B2 | 4/2011 | Li et al. | |
| 2003/0114897 A1 | 6/2003 | Von Arx et al. | |
| 2004/0106967 A1 | 6/2004 | Von Arx et al. | |
| 2004/0212496 A1 | 10/2004 | Villaseca et al. | |
| 2004/0260363 A1 | 12/2004 | Arx et al. | |
| 2005/0001742 A1* | 1/2005 | Small | 340/988 |
| 2005/0222629 A1 | 10/2005 | Perschbacher et al. | |
| 2005/0283208 A1 | 12/2005 | Von Arx et al. | |
| 2006/0009818 A1 | 1/2006 | Von Arx et al. | |
| 2006/0030903 A1 | 2/2006 | Seeberger et al. | |
| 2006/0111054 A1 | 5/2006 | Pan et al. | |
| 2006/0111643 A1 | 5/2006 | Cazares et al. | |
| 2006/0161223 A1 | 7/2006 | Vallapureddy et al. | |
| 2006/0194615 A1 | 8/2006 | Vallapureddy et al. | |
| 2006/0195161 A1 | 8/2006 | Li et al. | |
| 2010/0045480 A1 | 2/2010 | Vallapureddy et al. | |
| 2011/0178577 A1 | 7/2011 | Li et al. | |

FOREIGN PATENT DOCUMENTS

| | | |
|---|---|---|
| EP | 0748071 A2 | 12/1996 |
| EP | 0808033 A2 | 11/1997 |
| EP | 0863620 A2 | 9/1998 |
| EP | 0889603 A2 | 1/1999 |
| JP | 04-151915 A | 5/1992 |
| JP | 04-207421 A | 7/1992 |
| JP | 5-284077 A | 10/1993 |
| JP | 6-013951 A | 1/1994 |
| JP | 06-303220 A | 10/1994 |
| JP | 08-340290 A | 12/1996 |
| JP | 9-121101 A | 5/1997 |
| JP | 9-261141 A | 10/1997 |
| JP | 2001-345746 A | 12/2001 |
| JP | 2002-246968 A | 8/2002 |
| JP | 2003-318792 A | 11/2003 |
| JP | 2005-039539 A | 2/2005 |
| WO | WO-2004/066834 A1 | 8/2004 |
| WO | WO-2005115541 A1 | 12/2005 |
| WO | WO-2006093766 A1 | 9/2006 |
| WO | WO-2006093964 A1 | 9/2006 |

OTHER PUBLICATIONS

"U.S. Appl. No. 11/068,476 (Non-Final Office Action mailed Jul. 5, 2007", 5 pgs.

"U.S. Appl. No. 11/068,476, Notice of Allowance mailed Feb. 21, 2008", 4 pgs.

"U.S. Appl. No. 11/068,476 Response filed Jan. 11, 2007 to Non-Final Office Action mailed Oct. 16, 2007", 18 pgs.

"U.S. Appl. No. 11/068,476 Response filed Nov. 16, 2007 to Non-Final Office Action mailed Aug. 16, 2007", 13 pages.

"U.S. Appl. No. 11/068,478, Response filed Mar. 17, 2008 to Non-Final Office Action mailed Dec. 17, 2007", 19 pgs.

"U.S. Appl. No. 11/068,478 Non-Final Office Action mailed Dec. 17, 2007", 15 pgs.

"Non-Final Office Action mailed Oct. 16, 2006 in U.S. Appl. No. 11/068,476", 9 pgs.

"Non-Final Office Action Mailed Aug. 16, 2007 in U.S. Appl. No. 11/068,476", 9 pgs.

"U.S. Appl. No. 11/068,476, Non Final Office Action mailed Apr. 4, 2007", 5 pgs.

"U.S. Appl. No. 11/068,478, Non Final Office Action mailed Jan. 2, 2009", 11 pgs.

"U.S. Appl. No. 11/068,478, Notice of Allowance mailed Jun. 9, 2009", 8 pgs.

"U.S. Appl. No. 11/068,478, Response filed Mar. 30, 2009 to Non Final Office Action mailed Jan. 2, 2009", 20 pgs.

"European Application Serial No. 06736412.5, Communication dated Oct. 10, 2007", 2 pgs.

"European Application Serial No. 06736412.5, Response filed Nov. 16, 2007 to Communication dated Oct. 10, 2007", 38 pgs.

"U.S. Appl. No. 11/068,478, Advisory Action mailed Sep. 16, 2008", 3 pgs.

"U.S. Appl. No. 11/068,478, Final Office Action mailed Jun. 2, 2008", 17 pgs.

"U.S. Appl. No. 11/068,478, Response filed Aug. 4, 2008 to Final Office Action mailed Jun. 2, 2008", 19 pgs.

"U.S. Appl. No. 11/068,478, Response filed Nov. 3, 2008 to Final Office Action mailed Jun. 2, 2008 and Advisory Action mailed Sep. 16, 2008", 17 pgs.

"European Application Serial No. 06720991.6, Communication mailed Mar. 30, 2010", 2 pgs.

"Japanese Patent Application Serial No. 2007-558134, Voluntary Amendment filed Feb. 17, 2009", (w/ English Translation), 31 pgs.

"U.S. Appl. No. 11/068,478, Corrected Notice of Allowance mailed Jun. 19, 2009", 4 pgs.

"U.S. Appl. No. 12/156,538, Non-Final Office Action mailed Jun. 28, 2010", 6 pgs.

"U.S. Appl. No. 12/156,538, Notice of Allowance mailed Dec. 8, 2010", 4 pgs.

"U.S. Appl. No. 12/156,538, Response filed Sep. 28, 2010 to Non-Final Office Action mailed Jun. 28, 2010", 9 pgs.

"European Application Serial No. 06720991.6, Response filed Oct. 7, 2010 to Office Action mailed Mar. 30, 2010", 17 pgs.

"International Application Serial No. PCT/US2006/007092, International Search Report mailed Aug. 17, 2006", 5 pgs.

"International Application Serial No. PCT/US2006/007092, Written Opinion mailed Aug. 17, 2006", 9 pgs.

"Japanese Application Serial No. 2007-558069, Office Action mailed Jun. 10, 2011", (w/ English Translation), 7 pgs.

"Japanese Application Serial No. 2007-558134, Office Action mailed Jun. 10, 2011", (w/ English Translation), 9 pgs.

"U.S. Appl. No. 12/604,254, Non Final Office Action mailed Nov. 2, 2011", 7 pgs.

"Japanese Application Serial No. 2007-558069, Office Action mailed Jan. 19, 2012", (w/ English Translation), 7 pgs.

"Japanese Application Serial No. 2007-558134, Office Action mailed Jan. 13, 2012", (w/ English Translation), 8 pgs.

"U.S. Appl. No. 12/604,254, Response filed Feb. 29, 2012 to Non Final Office Action mailed Nov. 2, 2011", 9 pgs.

"U.S. Appl. No. 12/604,254, Notice of Allowance mailed Mar. 30, 2012", 5 pgs.

"Japanese Application Serial No. 2007-558069, Response filed Sep. 5, 2011 to Office Action dated Jun. 10, 2011", (w/ English Translation of Amended Claims), 12 pgs.

"Japanese Application Serial No. 2007-558134, Response filed Aug. 31, 2011 to Office Action dated Jun. 10, 2011", (w/ English Translation of Amended Claims), 33 pgs.

"Japanese Application Serial No. 2007-558069, Office Action mailed Aug. 8, 2012", (w/ English Translation), 12 pgs.

* cited by examiner

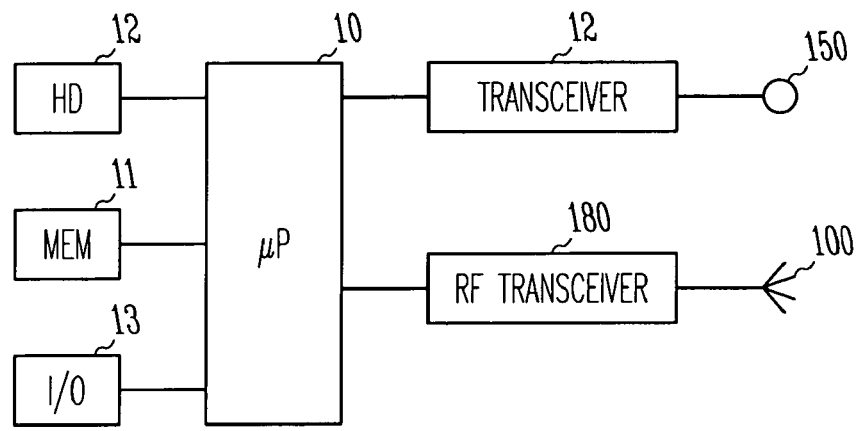
*Fig. 1*
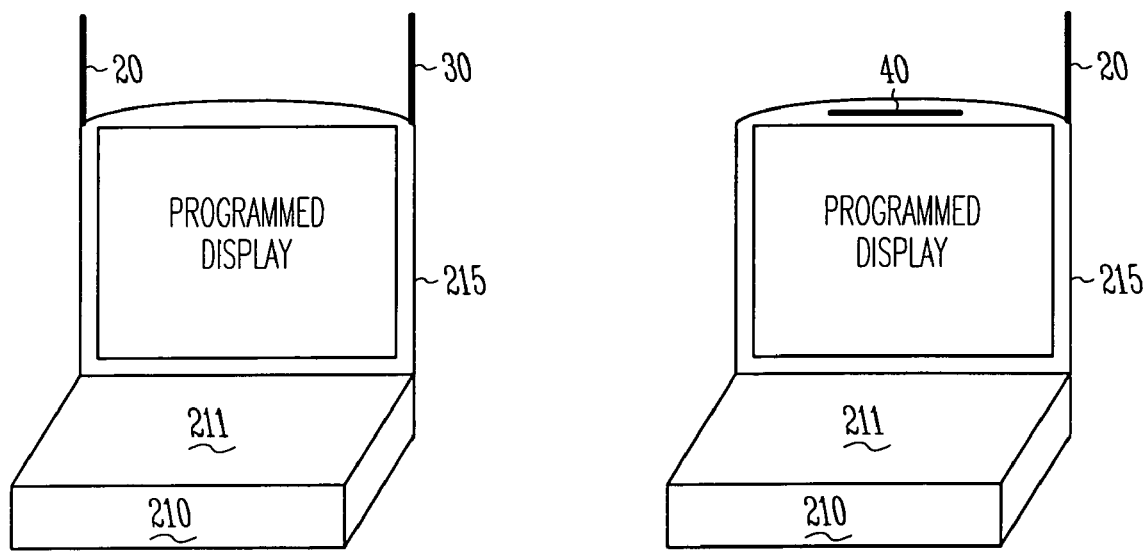
*Fig. 2*  *Fig. 3*

DIVERSITY ANTENNA SYSTEM FOR COMMUNICATION WITH AN IMPLANTABLE MEDICAL DEVICE

CROSS-REFERENCE TO RELATED APPLICATION

This application is related to commonly assigned, U.S. patent application Ser. No. 11/068,476, entitled "METHOD AND APPARATUS FOR OPERATING A DIVERSITY ANTENNA SYSTEM COMMUNICATING WITH IMPLANTABLE MEDICAL DEVICE" filed on Feb. 28, 2005, now issued as U.S. Pat. No. 7,392,092, which is hereby incorporated by reference in its entirety.

FIELD OF THE INVENTION

This invention pertains to implantable medical devices such as cardiac pacemakers and implantable cardioverter/defibrillators.

BACKGROUND

Implantable medical devices (IMDs), including cardiac rhythm management devices such as pacemakers and implantable cardioverter/defibrillators, typically have the capability to communicate data with an external device (ED) via a radio-frequency telemetry link. One such external device is an external programmer used to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data that may typically be telemetered from an implantable device are various operating parameters and physiological data, the latter either collected in real-time or stored from previous monitoring operations. An external device may also be a remote monitoring unit which collects data from the implantable device and transmits it over a network to a data gathering center.

External programmers are commonly configured to communicate with an IMD over an inductive link. Coil antennas in the external programmer and the IMD are inductively coupled so that data can be transmitted by modulating a carrier waveform which corresponds to the resonant frequency of the two coupled coils. An inductive link is a short-range communications channel requiring that the coil antenna of the external device be in close proximity to the IMD, typically within a few inches. Other types of telemetry systems may utilize far-field radio-frequency (RF) electromagnetic radiation to enable communications between an MD and an ED over a wireless medium. Such long-range RF telemetry allows the IMD to communicate with an ED, such as an external programmer or remote monitor, without the need for close proximity.

Communications via far-field RF telemetry, however, can be hindered by the effects of multi-path distortion which result in nulls in the transmission pattern of either the external device or the implantable device. In a typical environment, reflections of a transmitted wave caused by walls and other objects result in a standing wave pattern. Areas where the standing wave pattern results in a low amplitude signal below the noise floor are referred to as nulls or null areas. When an external programmer antenna is in a null with respect to an implantable device antenna, the RF link is lost and further communications are not possible. Because a patient may typically be moving around during telemetry sessions, such nulls may be transient and of short duration. Even short-duration nulls, however, cause difficulties when collecting certain types of data from an implantable device such as real-time electrograms.

SUMMARY

The present disclosure relates to a system for communicating with an implantable medical device via RF telemetry which mitigates the effects of nulls caused by, e.g., multi-path distortion. In one embodiment, signals transmitted by the implantable device to an external device are simultaneously received with a pair of separate spaced apart first and second antennas. The antennas may provide spatial and/or polar diversity. The presence of nulls in the implantable device's transmission pattern can be determined by detecting an error rate in the signals received from the implantable device with each antenna.

BRIEF DESCRIPTION OF THE DRAWINGS

FIG. 1 is a block diagram of the basic components of an external device.

FIG. 2 illustrates an exemplary antenna configuration for an external programmer which provides spatial diversity.

FIG. 3 illustrates an exemplary antenna configuration for an external programmer which provides both spatial and polar diversity.

DETAILED DESCRIPTION

Figure 4:
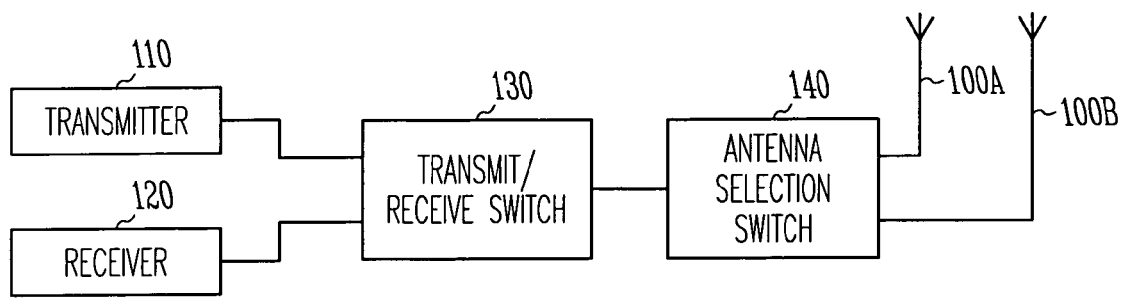
FIG. 4 illustrates an exemplary scheme for operating a diversity antenna with one receive path.

FIG. 1 shows a basic block diagram of an external device configured for communicating with an implantable medical device, where the external device may be either an external programmer or a remote monitoring device. In this exemplary embodiment, the external device includes a microprocessor 10, memory 11, and a hard disk 12 for data and program storage that supervises overall device operation as well as telemetry. Code executed by the microprocessor may be used to control the operation of the various telemetry components to be described below. User input/output devices 13, such as a keyboard and display, are interfaced to the microprocessor in order to enable a user such as a clinician to direct the operation of the external device. To provide telemetry, a long-range RF transceiver 180 which includes components for transmitting and receiving RF signals is interfaced to the microprocessor 10. The transmitter and receiver components are coupled to an antenna array 100 through one or more transmit/receive switch. The transmit/receive switches are controlled by the microprocessor and either passes radio-frequency signals from the transmitter to the antenna or from the antenna to the receiver to establish an RF link. As explained below, the antenna array 100 may comprise two or more antennas to form a diversity antenna. To effect communications between the devices over the RF link, a radio-frequency carrier signal modulated with digital data is transmitted wirelessly from one antenna to the other. A demodulator for extracting digital data from the carrier signal is incorporated into the receiver, and a modulator for modulating the carrier signal with digital data is incorporated into the transmitter. The interface to the microprocessor for the RF transmitter and receiver enables data transfer by the microprocessor. FIG. 1 also shows an inductively coupled transmitter/receiver 140 and antenna 150 by which communication may take place over an inductive link when the external and implantable devices are in close physical proximity to one another.

A diversity antenna is an array of two or more antennas separated in space to resulting spatial diversity and/or differing in polarity to result in polar diversity. FIG. 2 illustrates one embodiment of a diversity antenna configuration for an external programmer. External programmers are typically designed as laptop computers which incorporate the necessary telemetry equipment for communicating with an implantable device. The external programmer in FIG. 2 includes a housing 210 for containing the electronic components such as those illustrated in FIG. 1. The housing 210 is connected to a hinging display screen 215 and has a keyboard 211 mounted thereon. In this embodiment, two dipole antennas designated 20 and 30 are shown as mounted on the sides of the display screen extending vertically from its top edge. Because the two antennas 20 and 30 are separated by the width of the display screen, this antenna configuration provides spatial diversity. That is, should one antenna be located in a null area of the implantable device's transmission pattern, it is likely that the other antenna is not so that reception can continue. Similarly, when transmitting to the implantable device, if the implantable device should be in a null area of one antenna, it is likely that it is not in a null area of the other antenna.

FIG. 3 illustrates another embodiment in which the antenna 20 extends vertically as in FIG. 2, but the other antenna 40 is embedded in the top edge of the display screen and oriented horizontally. This antenna configuration provides spatial diversity due to the separation of the two antennas and also provides polar diversity because the two antennas are oriented differently. A monopole or dipole antenna is a linearly polarizing antenna which radiates electromagnetic waves which are polarized in the direction of the antenna's orientation. Such an antenna also most sensitively receives electromagnetic radiation which is polarized in the same direction as the antenna's orientation and is not sensitive at all to radiation polarized orthogonally to it. The antenna of an implantable medical device is usually a dipole or monopole antenna which, for example, extends from the implantable device housing or is incorporated into an intravenous lead. The waveform transmitted by the implantable device is therefore polarized in a direction which depends upon the position of the patient. Furthermore, the polarization of the transmitted waveform can change as the patient moves. The vertically oriented antenna 20 and the horizontally oriented antenna 40, being orthogonal to one another, provide polar diversity since an arbitrarily polarized waveform will be sensitively received by at least one of the antennas. Similarly, at least one of the antennas 20 or 40 will be capable of transmitting a waveform with a polarization that can be sensitively received by the implantable device antenna regardless of the latter's orientation.

Different schemes may be employed to operate a diversity antenna. In one embodiment, as illustrated by FIG. 4, an antenna selection switch 140 operated by the microprocessor 10 is located between the transmit/receive switch 130 and two antennas 100a and 100b, where the transmit/receive switch is connected to a transmitter 110 and a receiver 120. The antennas 100a and 100b may, for example, correspond to either the antennas 20 and 30 or to antennas 20 and 40 in FIGS. 2 and 3, respectively. The antenna selection switch 140 is operated by the microprocessor so that only one of the antennas 100a or 100b is active at a time by being connected to either the transmitter 110 or the receiver 120. In an exemplary scheme, the microprocessor selects one of the antennas for use in both transmission and reception and connects that antenna to the transmit/receive switch through the antenna selection switch. The microprocessor is then programmed to perform error detection on the signal received from the implantable device to determine if the currently used antenna may be in a null area. For example, a cyclic redundancy check applied to each received frame after digitization of the received signal. If the error rate exceeds a specified threshold, the microprocessor switches to the other antenna for both reception and transmission.

Figure 5:
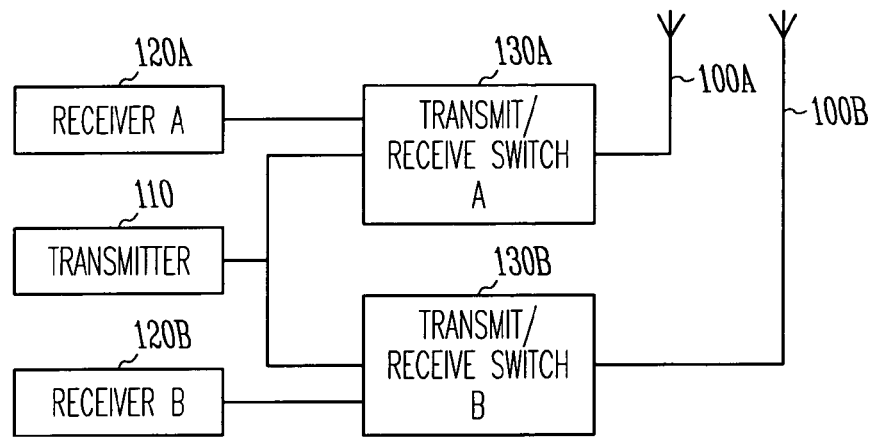
FIG. 5 illustrates an exemplary scheme for operating a diversity antenna with a dual receive path.

FIG. 5 illustrates another scheme for operating a diversity antenna in which both of the antennas 100a and 100b are active during reception by being connected to separate receivers 120a and 120b. In this embodiment, the receivers 120a and 120b are connected to antennas 100a and 100b by transmit/receive switches 130a and 130b, respectively. The two transmit/receive switches allow the device to receive signals from both antennas simultaneously but to use only one antenna at a time for transmission. During reception, the dual receive path allows the signal from both antennas to be monitored simultaneously in order to derive an error rate and determine if one of the antennas may be in a null area. For example, the signal from each antenna may be digitized, and a cyclic redundancy check then applied to each received frame from both signal paths. The device may use the data derived from either signal if no errors are present. For example, the device may simply use the data received from the antenna presently selected for transmitting unless an error is discovered in that signal. If the error rate exceeds a specified threshold in the antenna currently being used for transmission, the microprocessor switches to the other antenna for subsequent transmissions. Simultaneous reception from both antennas thus eliminates the need for retransmission of data by the implantable device should one antenna be in a null while the other is not. Also, since whether or not the alternate antenna is in a null is determined at the same time, switching to the alternate antenna may be performed more rapidly without requiring a retry for that antenna. Although two separate transmit/receive switches are used to allow only one antenna to be selected for transmitting, there is no need for an antenna selection switch as in the previously described embodiment.

Figure 6:
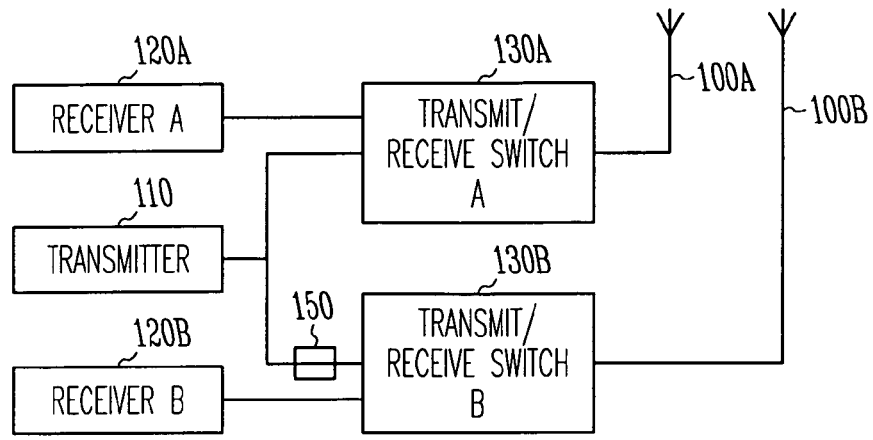
FIG. 6 illustrates an exemplary scheme for operating a diversity antenna which provides polar transmission diversity.

FIG. 6 illustrates another scheme for operating a diversity antenna which provides polar diversity such as illustrated in FIG. 3. The configuration of the transmitter 110, receivers 120a and 120b, transmit/receive switches 130a and 130b, and antennas 100a and 100b is identical to that of FIG. 5 except that a 90 degree phase shifter 150 is inserted in the transmission paths between the transmitter 110 and the transmit/receive switch 130a. Such a phase shifter may simply be a delay element which results in a 90 degree phase lag at the transmitting frequency. If both transmit/receive switches are switched on so that both antennas are driven at the same time by the transmitter, the result is a circularly polarized waveform. A circularly polarized waveform comprises two orthogonally polarized waveforms with a 90 degree phase difference between them. It may be desirable to transmit such a waveform when it is not known what the orientation of the implantable device's antenna is, such as when the external device is initiating communications, so that the transmitted waveform will have a component which is assured to be received by the implantable device's antenna. Although ideally a circularly polarized waveform is desired to provide this type of transmission diversity, an elliptically polarized waveform produced by a phase shift in one of the 90 transmitted waveforms which is greater or lesser than 90 degrees may provide the same benefits. Such elliptical polarization may result, for example, should the transmission frequency change such as occurs with frequency-hopping spread spectrum techniques.

The embodiments described above have been discussed primarily with reference to an external programmer. It should be appreciated, however, that those embodiments could be incorporated into any kind of external device which is configured to communicate with an implantable medical device, including a remote monitor.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. An external device for communicating with an implantable medical device, comprising:
   an antenna array for communicating with the implantable medical device, the antenna array including a first antenna segment and a second antenna segment, the second antenna segment separate from the first antenna segment;
   a microprocessor with associated memory for program and data storage;
   an RF transmitter interfaced to the microprocessor and connected to the first antenna segment through a first transmit/receive switch and connected to the second antenna segment through a second transmit/receive switch;
   a first receiver interfaced to the microprocessor and connected to the first antenna segment through a first transmit/receive switch;
   a second receiver interfaced to the microprocessor and connected to the second antenna segment through a second transmit/receive switch;
   wherein the microprocessor is programmed to:
      operate the first and second transmit/receive switches such that both receivers are connected to their respective antenna segments to simultaneously receive the same data communicated from the implantable medical device; and
      operate the first and second transmit/receive switches such that the RF transmitter is connected to both antenna segments to simultaneously transmit the same data to the implantable medical device.

2. The device of claim 1 wherein the first and second antenna segments are dipole antennas spaced apart in order to provide spatial diversity.

3. The device of claim 1 wherein the first and second antenna segments are dipole antennas oriented orthogonally to provide polar diversity.

4. The device of claim 1 further comprising:
   a display screen; and,
   wherein each of the antenna segments extends vertically from opposite sides of the display screen.

5. The device of claim 1 further comprising:
   a display screen; and,
   wherein one of the antenna segments is oriented horizontally and embedded in a top edge of the display screen, and the other extends vertically from a side of the display screen.

6. The device of claim 1 wherein the microprocessor is programmed such that the transmitter is connected to only one selected antenna segment during transmission of data to the implantable medical device.

7. The device of claim 6 wherein the microprocessor is programmed to detect an error rate in data received from each of the first and second antenna segments and, if the error rate for one antenna segment exceeds a specified threshold, switch to the other antenna segment for transmitting data to the implantable medical device.

8. The device of claim 7 wherein the microprocessor is programmed to detect an error rate by performing a cyclic redundancy check on each received frame after digitization of the received signal from the first and second antenna segments.

9. The device of claim 1 further comprising a phase shifter in the transmission path between the transmitter and the first transmit/receive switch, wherein the first and second antennas are oriented approximately orthogonally to one another, and wherein the microprocessor is programmed such that the transmitter is connected to both antenna segments during transmission of data to the implantable medical device.

10. The device of claim 9 wherein the phase shifter is a delay element.

11. The device of claim 9 wherein the phase shifter causes a 90 degree phase lag so that a circularly polarized waveform is transmitted to the implantable device.

12. An external device for communicating with an implantable medical device, comprising:
   a display screen;
   an antenna array for communicating with the implantable medical device, the signal antenna array including a first antenna segment oriented horizontally with respect to a top edge of the display screen and a second antenna segment oriented vertically with respect to a side edge of the display screen, the second antenna segment separate from the first antenna segment;
   a microprocessor with associated memory for program and data storage;
   an RF transmitter interfaced to a microprocessor and connected to the first antenna segment through a first transmit/receive switch and connected to the second antenna segment through a second transmit/receive switch;
   a first receiver interfaced to the microprocessor and connected to the first antenna segment through the first transmit/receive switch;
   a second receiver interfaced to the microprocessor and connected to the second antenna segment through the second transmit/receive switch;
   wherein the microprocessor is programmed to:
      operate the first and second transmit/receive switches such that both receivers can be connected to their respective antenna segments to simultaneously receive the same data communicated from the implantable medical device; and
      operate the first and second transmit/receive switches such that the RF transmitter is connected to both antenna segments to simultaneously transmit the same data to the implantable medical device.

13. The device of claim 12 wherein the second antenna segment is spaced apart from and orthogonal to the first antenna segment, providing spatial and polar diversity.

14. The device of claim 12 wherein the first antenna segment includes a first dipole antenna and the second antenna segment includes a second dipole antenna, separate from the first dipole antenna.

15. The device of claim 12 wherein the microprocessor is programmed such that the transmitter is connected to only one selected antenna segment during transmission of data to the implantable medical device.

16. The device of claim 15 wherein the microprocessor is programmed to detect an error rate in data received from each of the first and second antenna segments and, if the error rate for one antenna segment exceeds a specified threshold, switch to the other antenna segment for transmitting data to the implantable medical device.

17. The device of claim 12 wherein the microprocessor is programmed to receive data from the implantable medical device using one of the first and second antenna segments, to detect an error rate in the received data, and, if the error rate exceeds a specified threshold, to switch to the other antenna segment for receiving data from the implantable medical device.

18. An antenna array for an external device configured to communicate with an implantable medical device, the antenna array consisting of:
 a first antenna segment oriented horizontally with respect to a top edge of an external device housing, the first antenna segment configured to couple the first antenna segment to an RF transmitter in a transmit mode and to a first receiver in a receive mode; and
 a second antenna segment oriented vertically with respect to a side edge of the external device housing, the second antenna segment spaced apart from and orthogonal to the first antenna segment, the second antenna segment configured to couple the second antenna segment to the RF transmitter in the transmit mode to transmit the same data as the first antenna and to a second receiver in a receive mode, the first and second antenna segments providing spatial and polar diversity.

19. The antenna array of claim 18 wherein the first and second antenna segments are configured to be simultaneously coupled the first and second receivers to receive the same data communicated from the implantable medical device.

20. The antenna array of claim 19, wherein one of the first or second antenna segments is configured to transmit data to the implantable medical device, the one of the first or second antenna segments selected using a detected error rate in the received data communicated from the implantable medical device.

* * * * *